United States Patent
Shima (10) Patent No.: US 9,945,797 B2
(45) Date of Patent: Apr. 17, 2018

(54) ANALYSIS METHOD FOR OBTAINING XPS AND AES AND ELEMENTS IN EACH CHEMICAL BONDING STATE AND X-RAY PHOTOELECTRON SPECTROSCOPE FOR SAME

(71) Applicant: JEOL Ltd., Tokyo (JP)

(72) Inventor: Masahide Shima, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 15/258,374

(22) Filed: Sep. 7, 2016

(65) Prior Publication Data

US 2017/0067837 A1    Mar. 9, 2017

(30) Foreign Application Priority Data

Sep. 7, 2015 (JP) .................................. 2015-175704

(51) Int. Cl.
| | | |
|---|---|---|
| G01N 23/227 | (2018.01) | |
| G01N 23/225 | (2018.01) | |
| G01N 23/223 | (2006.01) | |

(52) U.S. Cl.
CPC ......... *G01N 23/223* (2013.01); *G01N 23/225* (2013.01); *G01N 23/227* (2013.01); *G01N 23/2273* (2013.01); *G01N 23/2276* (2013.01)

(58) Field of Classification Search
None
See application file for complete search history.

(56) References Cited

U.S. PATENT DOCUMENTS

| | | | | |
|---|---|---|---|---|
| 2007/0010973 | A1* | 1/2007 | deCecco | ................... H03F 1/26 |
| | | | | 702/189 |
| 2013/0016813 | A1* | 1/2013 | Yamazui | ............ G01N 23/2273 |
| | | | | 378/64 |

FOREIGN PATENT DOCUMENTS

JP        200985859 A      4/2009

OTHER PUBLICATIONS

Fantauzzi et al., "Exploiting XPS for the identification of sulfides and polysulfides", RSC Adv. 5, 75953 (2015).*
Ingo et al., "XPS studies of SiO2—TiO2 powders prepared by sol-gel process", Applied Surface Science, vols. 70-71, Part 1, 230-234 (1993).*
Extended European Search Report re EP 16187259.3 dated Dec. 22, 2016.

(Continued)

*Primary Examiner* — Wyatt Stoffa
*Assistant Examiner* — James Choi
(74) *Attorney, Agent, or Firm* — The Webb Law Firm (57) ABSTRACT

An analysis method includes: acquiring a photoelectron spectrum and an X-ray-excited Auger spectrum, the photoelectron spectrum being obtained by detecting photoelectrons emitted from a specimen by irradiating the specimen with X-rays, and the X-ray-excited Auger spectrum being obtained by detecting Auger electrons emitted from the specimen by irradiating the specimen with X-rays; calculating a quantitative value of each element included in the specimen based on the photoelectron spectrum; and performing a curve fitting process on the X-ray-excited Auger spectrum by using an electron beam-excited Auger electron standard spectrum, and calculating a quantitative value of an analysis target element in each chemical bonding state included in the specimen.

4 Claims, 5 Drawing Sheets

(56) References Cited

OTHER PUBLICATIONS

Grasso et al., X-ray photoemission spectra and x-ray excited Auger spectrum investigation of the electronic structure of Pd3(PS4)2, J. Vac. Sci. Technol., Jul./Aug. 2003, pp. 860-865, vol. A 21(4), American Vacuum Society.

Elsener et al., Electroless deposited Ni-P alloys: corrosion resistance mechanism, J Appl Electrochem, 2008, pp. 1053-1060, vol. 38, Springer Science+Business Media B.V.

Ingo et al., XPS studies of SiO2—TiO2 powders prepared by sol-gel process, Applied Surface Science, 1993, pp. 230-234, vol. 70/710, Elsevier Science Publishers B.V.

Fantauzzi et al., Exploiting XPS for the identification of sulfides and polysulfides, RSC Advances, 2015, pp. 75953-75963, vol. 5, The Royal Society of Chemistry.

* cited by examiner

C1s BINDING ENERGY [eV]

FIG.3

O1s BINDING ENERGY [eV]

ANALYSIS METHOD FOR OBTAINING XPS AND AES AND ELEMENTS IN EACH CHEMICAL BONDING STATE AND X-RAY PHOTOELECTRON SPECTROSCOPE FOR SAME

Japanese Patent Application No. 2015-175704, filed on Sep. 7, 2015, is hereby incorporated by reference in its entirety.

BACKGROUND OF THE INVENTION

The present invention relates to an analysis method and an X-ray photoelectron spectroscope.

An X-ray photoelectron spectroscope (XPS) and an Auger electron microscope (AES) are known as a device that is used to analyze the surface of a solid.

The X-ray photoelectron spectroscope is configured so that photoelectrons emitted from a specimen upon irradiation with X-rays are decelerated and focused on an analyzer by an input lens, and the energy of the photoelectrons are analyzed by the analyzer to obtain a photoelectron spectrum from the specimen.

The photoelectron spectrum obtained by the X-ray photoelectron spectroscope is normally represented by a mixed Gaussian/Lorentzian function (particularly when the analysis target is a light element). In this case, each peak in the photoelectron spectrum corresponds to the chemical bonding state, and the area of each peak is proportional to the relative proportion of the chemical bonding state. Therefore, the quantitative value of the element in each chemical bonding state can be obtained by performing a curve fitting calculation process on the photoelectron spectrum (see JP-A-2009-085859, for example).

The photoelectron spectrum of a light element is normally represented by a mixed Gaussian/Lorentzian function (see above). The photoelectron spectrum of a light element is characterized in that only the position of each peak in the spectrum is shifted even when the chemical bonding state has changed. Therefore, the curve fitting calculation process that uses a mixed Gaussian/Lorentzian function can be appropriately performed on the photoelectron spectrum of a light element.

However, the photoelectron spectrum of a metal that belongs to the fourth or higher period of the periodic table (e.g., transition metal) cannot be appropriately represented by a mixed Gaussian/Lorentzian function. Since the photoelectron spectrum of a transition metal is characterized in that the shift amount of each peak is small when the chemical bonding state has changed, it is difficult to apply the curve fitting process to the photoelectron spectrum of a transition metal.

SUMMARY

Several aspects of the invention may provide an analysis method and an X-ray photoelectron spectroscope that can accurately analyze even a metal that belongs to the fourth or higher period of the periodic table.

According to a first aspect of the invention, there is provided an analysis method including:

acquiring a photoelectron spectrum and an X-ray-excited Auger spectrum, the photoelectron spectrum being obtained by detecting photoelectrons emitted from a specimen by irradiating the specimen with X-rays, and the X-ray-excited Auger spectrum being obtained by detecting Auger electrons emitted from the specimen by irradiating the specimen with X-rays;

calculating a quantitative value of each element included in the specimen based on the photoelectron spectrum; and performing a curve fitting process on the X-ray-excited Auger spectrum by using an electron beam-excited Auger electron standard spectrum, and calculating a quantitative value of an analysis target element in each chemical bonding state included in the specimen.

According to a second aspect of the invention, there is provided an X-ray photoelectron spectroscope including:

a spectrum acquisition section that acquires a photoelectron spectrum and an X-ray-excited Auger spectrum, the photoelectron spectrum being obtained by detecting photoelectrons emitted from a specimen by irradiating the specimen with X-rays, and the X-ray-excited Auger spectrum being obtained by detecting Auger electrons emitted from the specimen by irradiating the specimen with X-rays;

a photoelectron spectrum analysis section that calculates a quantitative value of each element included in the specimen based on the photoelectron spectrum; and a chemical bonding state analysis section that performs a curve fitting process on the X-ray-excited Auger spectrum by using an electron beam-excited Auger electron standard spectrum, and calculates as quantitative value of an analysis target element in each chemical bonding state included in the specimen.

DETAILED DESCRIPTION OF THE EMBODIMENT (1) According to one embodiment of the invention, an analysis method includes:

acquiring a photoelectron spectrum and an X-ray-excited Auger spectrum, the photoelectron spectrum being obtained by detecting photoelectrons emitted from a specimen by irradiating the specimen with X-rays, and the X-ray-excited Auger spectrum being obtained by detecting Auger electrons emitted from the specimen by irradiating the specimen with X-rays;

calculating a quantitative value of each element included in the specimen based on the photoelectron spectrum; and performing a curve fitting process on the X-ray-excited Auger spectrum by using an electron beam-excited Auger electron standard spectrum, and calculating a quantitative value of an analysis target element in each chemical bonding state included in the specimen.

Since the analysis method calculates the quantitative value of the analysis target element in each chemical bonding state included in the specimen by performing the curve fitting process on the X-ray-excited Auger spectrum by using the electron beam-excited Auger electron standard spectrum, it is possible to accurately calculate the quantitative value of the analysis target element in each chemical bonding state even when the analysis target element is a metal that belongs to the fourth or higher period of the periodic table.

(2) In the analysis method, the calculating of the quantitative value of the analysis target element in each chemical bonding state may perform the curve fitting process on the X-ray-excited Auger spectrum by using the electron beam-excited Auger electron standard spectrum, and calculate the quantitative value of the analysis target element in each chemical bonding state when the analysis target element is a metal that belongs to the fourth or higher period.

This makes it possible to accurately calculate the quantitative value of the analysis target element in each chemical bonding state even when the analysis target element is a metal that belongs to the fourth or higher period of the periodic table.

(3) In the analysis method, the calculating of the quantitative value of the analysis target element in each chemical bonding state may include:

performing the curve fitting process on the X-ray-excited Auger spectrum by using the electron beam-excited Auger electron standard spectrum, and calculating an abundance ratio of the analysis target element in each chemical bonding state; and calculating the quantitative value of the analysis target element in each chemical bonding state based on the abundance ratio of the analysis target element in each chemical bonding state, and the quantitative value of each element included in the specimen.

This makes it possible to calculate the quantitative value of the analysis target element in each chemical bonding state from the X-ray-excited Auger spectrum.

(4) According to another embodiment of the invention, an X-ray photoelectron spectroscope includes:

a spectrum acquisition section that acquires a photoelectron spectrum and an X-ray-excited Auger spectrum, the photoelectron spectrum being obtained by detecting photoelectrons emitted from a specimen by irradiating the specimen with X-rays, and the X-ray-excited Auger spectrum being obtained by detecting Auger electrons emitted from the specimen by irradiating the specimen with X-rays;

a photoelectron spectrum analysis section that calculates a quantitative value of each element included in the specimen based on the photoelectron spectrum; and a chemical bonding state analysis section that performs a curve fitting process on the X-ray-excited Auger spectrum by using an electron beam-excited Auger electron standard spectrum, and calculates a quantitative value of an analysis target element in each chemical bonding state included in the specimen.

Since the X-ray photoelectron spectroscope is configured so that the chemical bonding state analysis section calculates the quantitative value of the analysis target element in each chemical bonding state included in the specimen by performing the curve fitting process on the X-ray-excited Auger spectrum by using the electron beam-excited Auger electron standard spectrum, it is possible to accurately calculate the quantitative value of the analysis target element in each chemical bonding state even when the analysis target element is a metal that belongs to the fourth or higher period of the periodic table.

The exemplary embodiments of the invention are described in detail below with reference to the drawings. Note that the following exemplary embodiments do not unduly limit the scope of the invention as stated in the claims. Note also that all of the elements described below should not necessarily be taken as essential elements of the invention.

1. X-Ray Photoelectron Spectroscope

Figure 1:
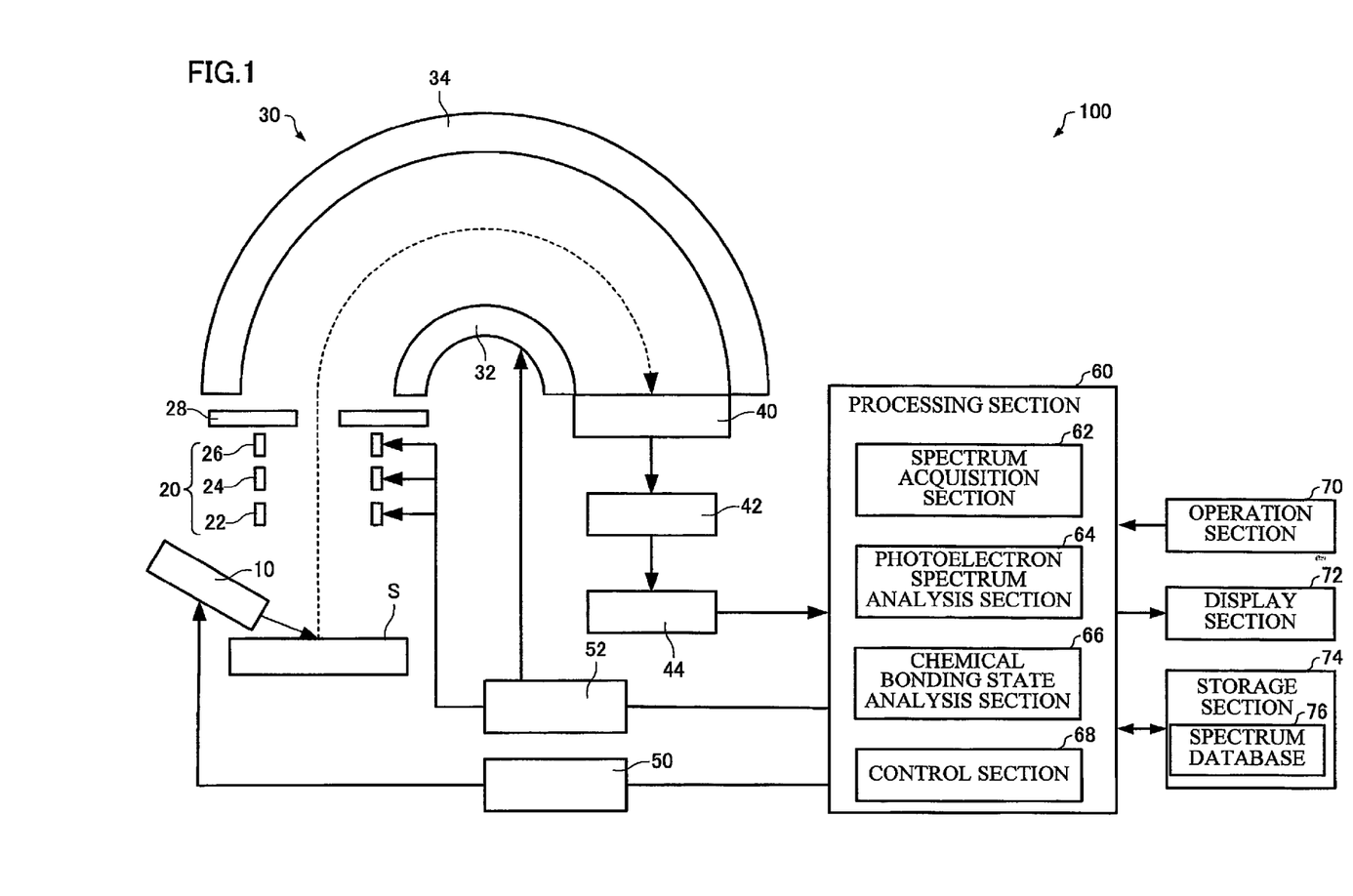
FIG. 1 schematically illustrates an X-ray photoelectron spectroscope according to one embodiment of the invention.

An X-ray photoelectron spectroscope according to one embodiment of the invention is described below with reference to the drawings. FIG. 1 schematically illustrates an X-ray photoelectron spectroscope 100 according to one embodiment of the invention.

As illustrated in FIG. 1, the X-ray photoelectron spectroscope 100 includes an X-ray source 10, an input lens 20, an energy analyzer section 30, a detector 40, power supply units 50 and 52, a processing section 60, an operation section 70, a display section 72, and a storage section 74.

The X-ray source 10 generates X-rays, and irradiates a specimen S with the X-rays. When the specimen S has been irradiated with the X-rays, photoelectrons, Auger electrons, and the like are emitted from the specimen S.

The input lens 20 includes an electrostatic lens 22, an electrostatic lens 24, and a deceleration lens 26. The electrostatic lens 22 and the electrostatic lens 24 focus electrons (photoelectrons and Auger electrons) on an entrance slit 28. The deceleration lens 26 decelerates electrons that enter the energy analyzer section 30, for example.

The entrance slit 28 is disposed at the entrance of the energy analyzer section 30. The entrance slit 28 limits the electrons that enter the energy analyzer section 30.

The energy analyzer section 30 analyzes the energy of the electrons emitted from the specimen S. The energy analyzer section 30 is an electrostatic hemispherical analyzer, for example. The energy analyzer, section 30 includes an inner hemispherical electrode 32 and an outer hemispherical electrode 34. A preset voltage is applied between the inner hemispherical electrode 32 and the outer hemispherical electrode 34, and the pass energy of electrons is determined by the preset voltage, for example.

The detector 40 detects the electrons whose energy were analyzed by the energy analyzer section 30. A signal output from the detector 40 is amplified by an amplifier 42, converted into a digital signal by an A/D converter 44, and transmitted to the processing section 60.

The X-ray photoelectron spectroscope 100 is provided with a constant analyzer energy (CAE) mode and a constant retarding ratio (CRR) mode.

In the CAE mode, the energy when the electrons emitted from the specimen S pass through the energy analyzer section 30 is always maintained to be constant (i.e., the pass energy is maintained to be constant) regardless of the kinetic energy of the electrons. In the CAE mode, the potential difference applied between the inner hemispherical electrode 32 and the outer hemispherical electrode 34 is set to a constant value, and the voltage applied to the deceleration lens 26 is swept. In the CAE mode, the energy resolution can be made identical with respect to all of the measured elements.

In the CRR mode, the electrons are decelerated at a constant ratio corresponding to the kinetic energy of the measurement target electrons. Specifically, the ratio $E_P/E_0$ is set to be constant. Note that $E_0$ is the electron energy, and $E_P$ is the pass energy. In the CRR mode, the potential difference applied between the inner hemispherical electrode 32 and the outer hemispherical electrode 34 is swept together with the voltage applied to the deceleration lens 26, and the energy of the electrons are analyzed at a constant deceleration rate. In the CRR mode, the energy resolution changes corresponding to the kinetic energy of electrons.

The power supply unit 50 transmits a control signal that causes the X-ray source 10 to generate X-rays based on an instruction output from a control section 68. The power supply unit 52 supplies a control voltage to the input lens 20 and the energy analyzer section 30 based on an instruction output from the control section 68.

The operation section 70 acquires an operation signal that corresponds to the operation performed by the user, and transmits the operation signal to the processing section 60. The function of the operation section 70 may be implemented by a button, a key, a touch panel display, or a microphone, for example.

The display section 72 displays an image generated by the processing section 60. The function of the display section 72 may be implemented by an LCD, a CRT, or the like.

The storage section 74 stores a program, data, and the like that cause or allow the processing section 60 to perform various calculation processes and control processes. The storage section 74 is used as a work area for the processing section 60, and temporarily stores the results of calculations and the like performed by the processing section 60 according to a program, for example. The function of the storage section 74 may be implemented by a hard disk, a RAM, or the like.

The storage section 74 stores the signal (output signal) (i.e., a photoelectron spectrum signal obtained by detecting photoelectrons, and an Auger spectrum signal obtained by detecting Auger electrons) output from the detector 40.

The storage section 74 stores a spectrum database 76 that stores the electron beam-excited Auger electron standard spectrum of each element. The standard spectrum stored in the spectrum database 76 is an Auger spectrum obtained by irradiating a known specimen with electron beams by using an Auger electron spectroscope, and detecting Auger electrons emitted from the specimen. The Auger spectrum is stored corresponding to each chemical bonding state of each element. The standard spectrum measurement conditions are also stored in the spectrum database 76. Examples of the measurement conditions stored in the spectrum database 76 include the illumination current, the accelerating voltage, the tilt angle of the stage, the pass energy, and the like.

Note that the X-ray photoelectron spectroscope 100 may receive the spectrum database 76 stored in an information storage medium or a storage section included in a server (not illustrated in the drawings) through a network, and store the received spectrum database 76 in the storage section 74.

The processing section 60 performs a process that controls each section of the X-ray photoelectron spectroscope 100, a process that acquires a photoelectron spectrum and an X-ray-excited Auger spectrum, and performs a quantitative calculation process, and the like. The function of the processing section 60 may be implemented by hardware such as a processor (e.g., CPU or DSP), or a program. The processing section 60 includes a spectrum acquisition section 62, a photoelectron spectrum analysis section 64, a chemical bonding state analysis section 66, and the control section 68.

The spectrum acquisition section 62 acquires the photoelectron spectra obtained by detecting the photoelectrons emitted from the specimen S by irradiating the specimen S with X-rays, and the X-ray-excited Auger spectra obtained by detecting the Auger electrons emitted from the specimen S by irradiating the specimen S with X-rays. The spectrum acquisition section 62 acquires the photoelectron spectrum by reading the photoelectron spectrum signal stored in the storage section 74. The spectrum acquisition section 62 acquires the Auger spectrum by reading the Auger spectrum signal stored in the storage section 74.

The photoelectron spectrum analysis section 64 calculates the quantitative value of each element included in the specimen S based on the photoelectron spectra acquired by the spectrum acquisition section 62. For example, the photoelectron spectrum analysis section 64 performs the quantitative calculation process based on the photoelectron spectrum by using a relative sensibility factor (RSF) method. The photoelectron spectrum analysis section 64 thus calculates the quantitative value of each element included in the specimen S. Note that the quantitative calculation process may be performed by a method other than the RSF method.

The chemical bonding state analysis section 66 analyzes the chemical bonding state of the analysis target element included in the specimen S. For example, when the analysis target element is a metal that belongs to the fourth or higher period of the periodic table, the chemical bonding state analysis section 66 performs the curve fitting process on the X-ray-excited Auger spectrum by using the electron beam-excited Auger electron standard spectrum, and calculates the abundance ratio of the analysis target element in each chemical bonding state in the specimen S. The chemical bonding state analysis section 66 performs the curve fitting calculation process on the X-ray-excited Auger spectrum acquired by the spectrum acquisition section 62 by using the standard spectrum read from the spectrum database 76 stored in the storage section 74. The abundance ratio of the analysis target element in each chemical bonding state included in the specimen S can thus be calculated.

The chemical bonding state analysis section 66 calculates the quantitative value of the analysis target element in each chemical bonding state included in the specimen S based on the abundance ratio of the analysis target element in each chemical bonding state included in the specimen S, and the quantitative value of each element included in the specimen S. Note that quantification of the intensity of X-ray-excited Auger electrons has not been formulated. Therefore, the chemical bonding state analysis section 66 calculates the quantitative value of the analysis target element in each chemical bonding state included in the specimen S by applying the abundance ratio of the analysis target element in each chemical bonding state included in the specimen S calculated by the curve fitting calculation process to the quantitative value of each element included in the specimen S that has been calculated by the photoelectron spectrum analysis section 64.

When the analysis target element included in the specimen S is not a metal that belongs to the fourth or higher period of the periodic table, the chemical bonding state analysis section 66 performs the curve fitting process on the photoelectron spectrum by using a trial function (e.g., mixed Gaussian/Lorentzian function). The position of each peak in the photoelectron spectrum corresponds to the chemical bonding state, and the area of each peak is proportional to the relative proportion of the chemical bonding state. Therefore, the chemical bonding state analysis section 66 can calculate the quantitative value of the analysis target element in each chemical bonding state included in the specimen S by performing the curve fitting process on the photoelectron spectrum.

Although an example in which whether or not the analysis target element included in the specimen S is a metal that belongs to the fourth or higher period of the periodic table is determined, has been described above, whether or not the analysis target element included in the specimen S is a transition metal may be determined, for example. An element on which the quantitative calculation process is performed by using the X-ray-excited Auger spectrum, and an element on which the quantitative calculation process is performed by using the photoelectron spectrum, may be set in advance, for example.

The control section 68 performs a process that transmits an instruction to the power supply unit 50 to irradiate the specimen S with X-rays, a process that transmits an instruction to the power supply unit 52 to supply the control voltage to the input lens 20 and the energy analyzer section 30, and the like.

2. Analysis Method

An analysis method that is implemented by the X-ray photoelectron spectroscope 100 according to one embodiment of the invention is described below with reference to the drawings.

The photoelectron spectrum measurement process (CAE mode) performed by the X-ray photoelectron spectroscope 100 is described below.

When the user has set the pass energy through the operation section 70, the operation section 70 transmits the operation signal including information about the pass energy set by the user to the processing section 60. When the processing section 60 has received the operation signal, the control section 68 transmits an instruction to the power supply unit 52 to apply a voltage (preset voltage) based on the pass energy set by the user between the inner hemispherical electrode 32 and the outer hemispherical electrode 34 of the energy analyzer section 30. The control section 68 also transmits an instruction to the power supply unit 52 to apply a sweep voltage that decelerates the photoelectrons introduced into the energy analyzer section 30 to the deceleration lens 26. The photoelectrons that have been emitted from the specimen S and differ in energy can be decelerated to have a constant energy corresponding to the pass energy set by the user, by applying the sweep voltage to the deceleration lens 26 (i.e., sweeping the voltage applied to the deceleration lens 26). The control section 68 further transmits an instruction to the power supply unit 50 to irradiate the specimen S with X-rays.

The X-ray source 10 generates X-rays based on the instruction, and the generated X-rays are applied to the specimen S. When the X-rays have been applied to the specimen S, photoelectrons that differ in energy are emitted from the specimen S. The photoelectrons that differ in energy are decelerated by the deceleration lens 26 to have a constant energy (corresponding to the pass energy set by the user), focused on the entrance slit 28 through the electrostatic lenses 22 and 24, and introduced into the energy analyzer section 30. The energy of the photoelectrons introduced into the energy analyzer section 30 are analyzed by the energy analyzer section 30, and the photoelectrons having the pass energy set by the user are detected by the detector 40.

The signal output from the detector 40 is transmitted to the processing section 60 through the amplifier 42 and the AD converter 44, and stored in the storage section 74 as a photoelectron spectrum signal while being linked to the sweep voltage.

The X-ray-excited Auger spectrum measurement process performed by the X-ray photoelectron spectroscope 100 is described below.

When the user has designated the analysis target element included in the specimen S through the operation section 70, and set the measurement conditions, the operation section 70 transmits the operation signal including information about the analysis target element designated by the user and information about the measurement conditions to the processing section 60. The measurement conditions are set to be consistent with the measurement conditions stored in the spectrum database 76. For example, the user sets the measurement conditions referring to the measurement conditions stored in the spectrum database 76 that is stored in the storage section 74. An example in which the X-ray photoelectron spectroscope 100 is set to the CRR mode is described below.

When the processing section 60 has received the operation signal, the control section 68 controls the power supply units 50 and 52 based on the measurement conditions set by the user. Specifically, the control section 68 transmits an instruction to the power supply unit 52 to sweep the potential difference applied between the inner hemispherical electrode 32 and the outer hemispherical electrode 34 of the energy analyzer section 30 together with the voltage applied to the deceleration lens 26. The Auger electrons can thus be decelerated at a constant rate corresponding to the kinetic energy of the measurement target Auger electrons. The control section 68 further transmits an instruction to the power supply unit 50 to irradiate the specimen S with X-rays.

The X-ray source 10 generates X-rays based on the instruction, and the specimen S is irradiated with generated X-rays. When the specimen S has been irradiated with X-rays, Auger electrons that differ in energy are emitted from the specimen S. The Auger electrons that differ in energy are decelerated by the deceleration lens 26 at a constant rate corresponding to the kinetic energy, focused on the entrance slit 28 through the electrostatic lenses 22 and 24, and introduced into the energy analyzer section 30. The energy of the Auger electrons introduced into the energy analyzer section 30 are analyzed by the energy analyzer section 30 at a constant deceleration rate, and detected by the detector 40.

The signal output from the detector 40 is transmitted to the processing section 60 through the amplifier 42 and the AD converter 44, and stored in the storage section 74 as an Auger spectrum signal while being linked to the sweep voltage.

The X-ray photoelectron spectroscope 100 thus measures the photoelectron spectrum and the Auger spectrum from the specimen S.

Figure 2:
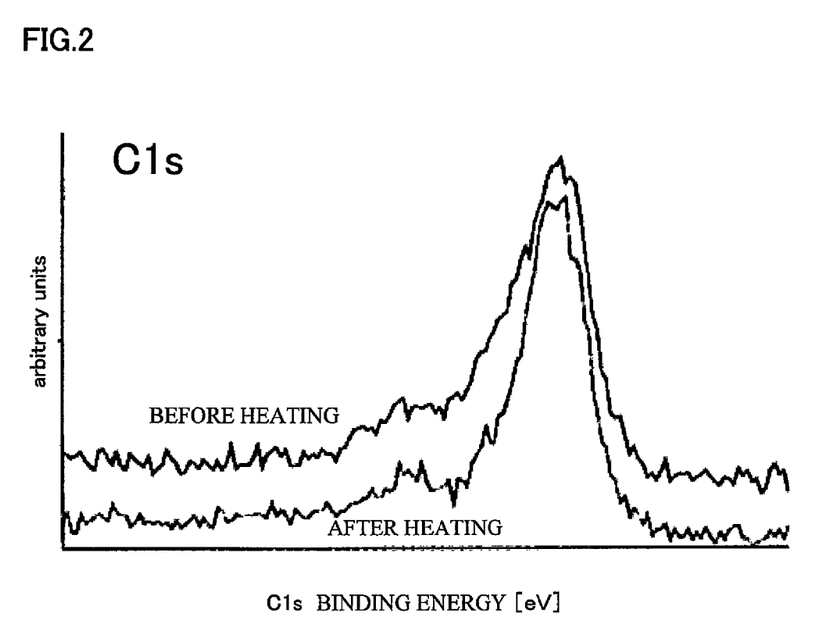
FIG. 2 is a graph illustrating a photoelectron spectrum measured by an X-ray photoelectron spectroscope according to one embodiment of the invention.
Figure 3:
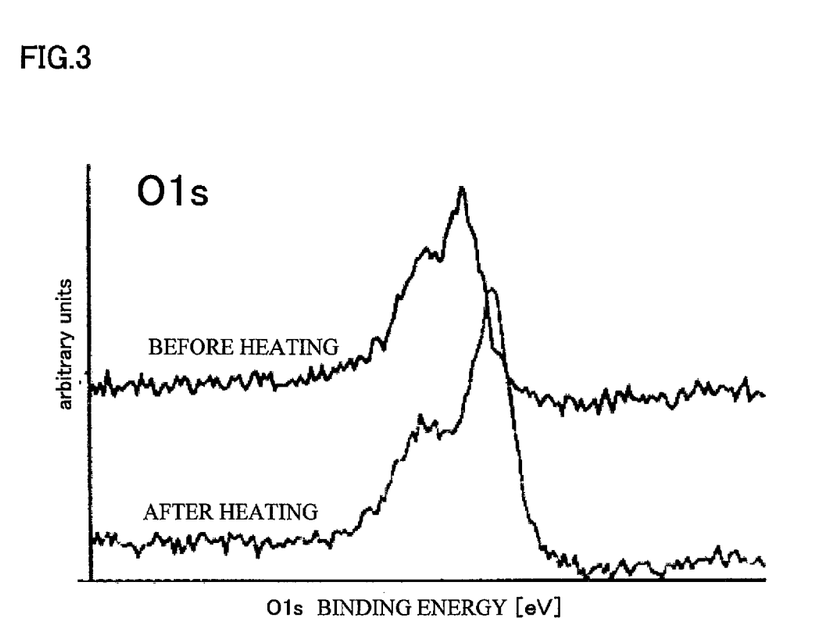
FIG. 3 is a graph illustrating a photoelectron spectrum measured by an X-ray photoelectron spectroscope according to one embodiment of the invention.
Figure 4:
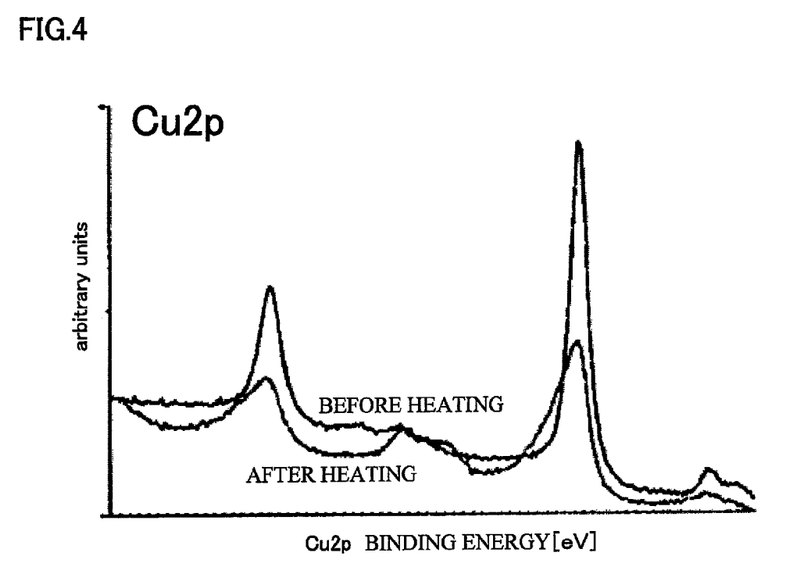
FIG. 4 is a graph illustrating a photoelectron spectrum measured by an X-ray photoelectron spectroscope according to one embodiment of the invention.
Figure 5:
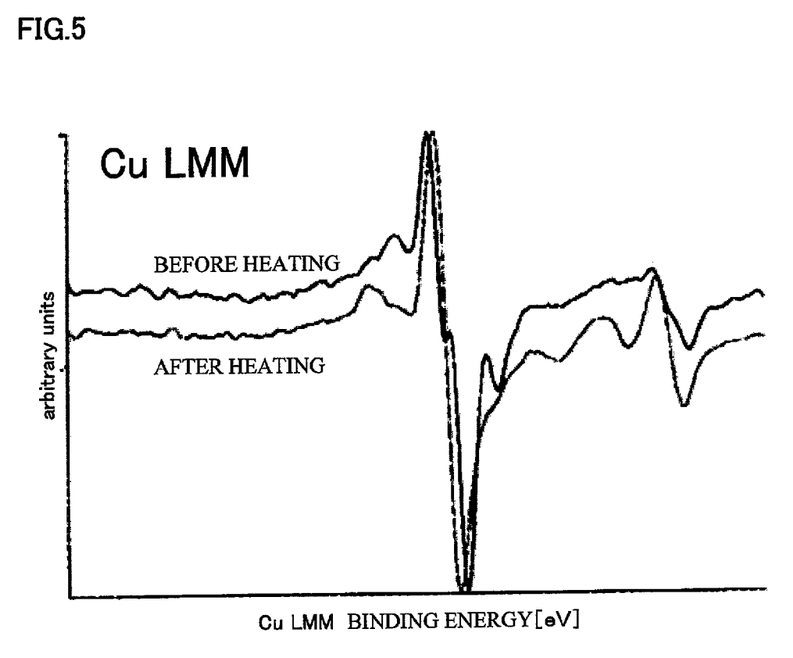
FIG. 5 is a graph illustrating an Auger spectrum measured by an X-ray photoelectron spectroscope according to one embodiment of the invention.

FIGS. 2 to 4 illustrate an example of the photoelectron spectrum measured by the X-ray photoelectron spectroscope 100 from the specimen S. FIG. 5 illustrates an example of the Auger spectrum measured by the X-ray photoelectron spectroscope 100 from the specimen S. Note that FIGS. 2 to 5 illustrate a case where the specimen S is a copper thin film that has not been heated ("BEFORE HEATING"), and a case where the specimen S is a copper thin film that has been heated ("AFTER HEATING").

The C1s spectra before and after heating the copper thin film (see FIG. 2), the O1s spectra before and after heating the copper thin film (see FIG. 3), the Cu2p spectra before and after heating the copper thin film (see FIG. 4), and the Auger spectra before and after heating the copper thin film (see FIG. 5), were obtained by the measurement process performed by the X-ray photoelectron spectroscope 100.

The Auger spectra illustrated in FIG. 5 were measured so that the measurement conditions were consistent with the measurement conditions stored in the spectrum database 76 (see above). Therefore, the energy resolution (pass energy) is consistent with that of the standard spectrum stored in the spectrum database 76. Therefore, the X-ray-excited Auger spectrum measured by the X-ray photoelectron spectroscope 100 from the specimen S approximately coincides in shape with the standard spectrum (electron beam-excited Auger spectrum).

Figure 6:
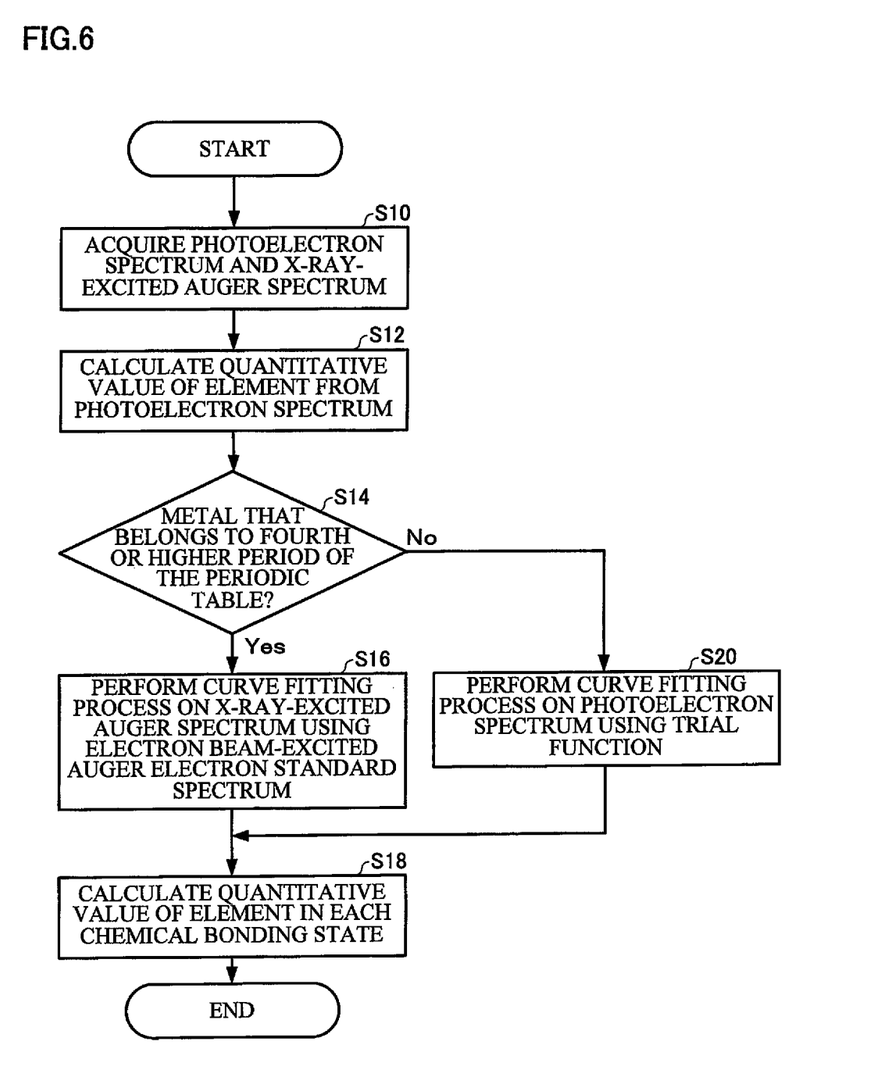
FIG. 6 is a flowchart illustrating an example of a process performed by a processing section in an X-ray photoelectron spectroscope according to one embodiment of the invention.

FIG. 6 is a flowchart illustrating an example of the process performed by the processing section 60 in the X-ray photoelectron spectroscope 100 according to one embodiment of the invention. An example in which the processing section 60 performs the quantitative calculation process by using the photoelectron spectra illustrated in FIGS. 2 to 4 and the Auger spectra illustrated in FIG. 5 (obtained from the specimen S), is described below.

The spectrum acquisition section 62 acquires the photoelectron spectra obtained by detecting the photoelectrons emitted from the specimen S by irradiating the specimen with X-rays, and the X-ray-excited Auger spectra obtained by detecting the Auger electrons emitted from the specimen S by irradiating the specimen with X-rays (step S10). The spectrum acquisition section 62 acquires the photoelectron spectra illustrated in FIGS. 2 to 4 by reading the photoelectron spectrum signal stored in the storage section 74. The spectrum acquisition section 62 acquires the Auger spectra illustrated in FIG. 5 by reading the Auger spectrum signal stored in the storage section 74.

The photoelectron spectrum analysis section 64 calculates the quantitative value of each element included in the specimen S based on the photoelectron spectra acquired by the spectrum acquisition section 62 (step S12). For example, the photoelectron spectrum analysis section 64 performs the quantitative calculation process based on the photoelectron spectra illustrated in FIGS. 2 to 4 by using a relative sensitivity factor (RSF) method.

The quantitative value of each element included in the specimen S calculated from the photoelectron spectra illustrated in FIGS. 2 to 4 is listed in Table 1.

TABLE 1

|  | C | O | Cu |
| --- | --- | --- | --- |
| Before heating | 31% | 23% | 46% |
| After heating | 40% | 35% | 25% |

The chemical bonding state analysis section 66 performs a process that determines whether or not the analysis target element included in the specimen S is a metal that belongs to the fourth or higher period of the periodic table (step S14). In this example, since Cu (i.e., analysis target element) is a metal that belongs to the fourth or higher period of the periodic table, it is determined that the analysis target element is a metal that belongs to the fourth or higher period of the periodic table.

When it has been determined that the analysis target element included in the specimen S is a metal that belongs to the fourth or higher period of the periodic table (Yes in step S14), the chemical bonding state analysis section 66 performs the curve fitting process on the X-ray-excited Auger spectrum by using the electron beam-excited Auger electron standard spectrum, and calculates the abundance ratio of the analysis target element in each chemical bonding state (step S16). The chemical bonding state analysis section 66 performs the curve fitting calculation process on the Auger spectrum of Cu illustrated in FIG. 5 by using the standard spectrum of Cu, the standard spectrum of $Cu_2O$, and the standard spectrum of CuO that have been read from the spectrum database 76 stored in the storage section 74.

Figure 7:
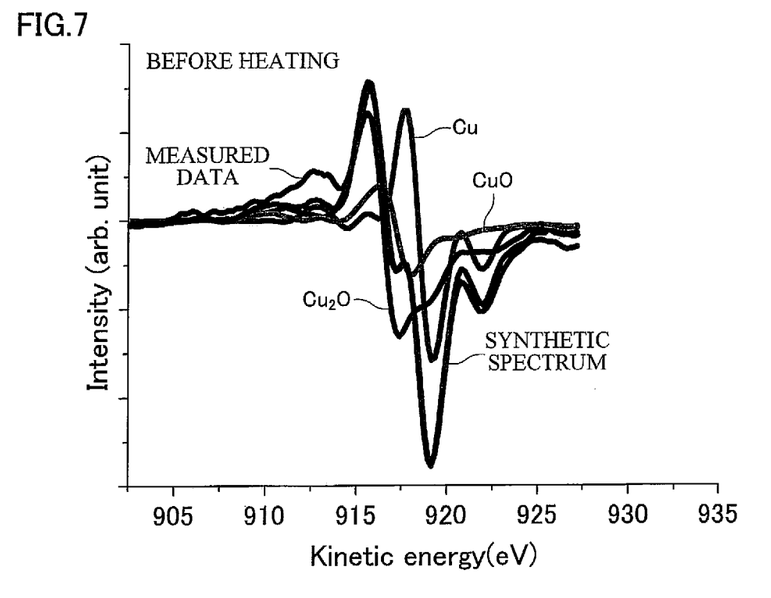
FIG. 7 is a graph illustrating a result of a curve fitting calculation process on an Auger spectrum obtained from a specimen before heating.
Figure 8:
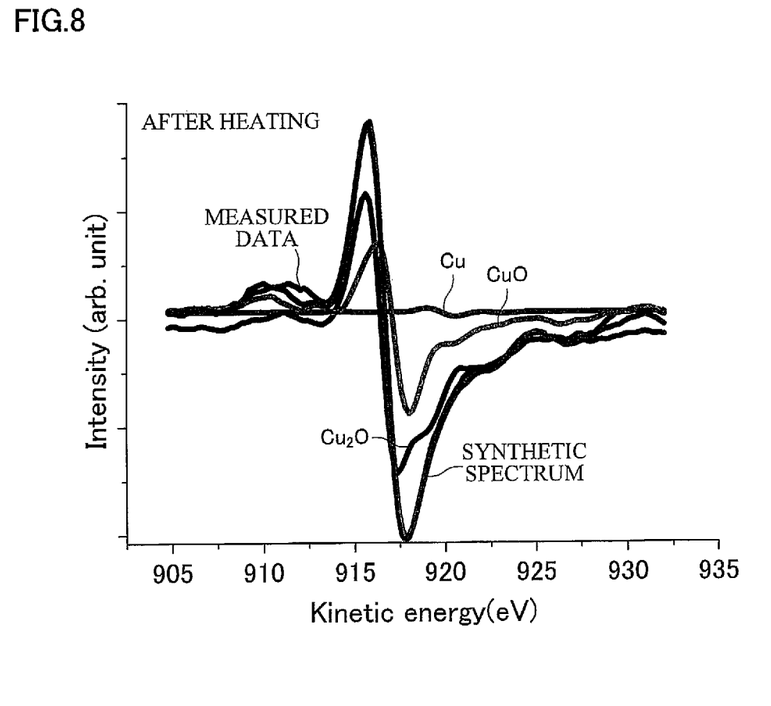
FIG. 8 is a graph illustrating a result of a curve fitting calculation process on an Auger spectrum obtained from a specimen after heating.

FIG. 7 illustrates the result of the curve fitting calculation process on the Auger spectrum obtained from the specimen S before heating. FIG. 8 illustrates the result of the curve fitting calculation process on the Auger spectrum obtained from the specimen S after heating.

When performing the curve fitting calculation process on the Auger spectrum obtained from the specimen S by using the standard spectrum, the standard spectrum of each chemical bonding state is normalized corresponding to the measurement conditions (e.g., the illumination current, the accelerating voltage, and the tilt angle of the stage) when the standard spectrum was measured. When the normalized standard spectrum (intensity) is used, the intensity of the spectrum corresponding to each chemical bonding state that has been subjected to the curve fitting calculation process represents a value that is proportional to the atomic concentration (i.e., the abundance ratio of an element in each chemical bonding state).

As illustrated in FIGS. 7 and 8, the Auger spectrum is used in differential form when performing the curve fitting calculation process. This makes it possible to disregard the difference in background intensity between the measured Auger spectrum and the standard spectrum.

The Auger spectrum obtained from the specimen S is an X-ray-excited Auger spectrum, and the standard spectrum is an electron beam-excited Auger spectrum. Therefore, the Auger spectrum obtained from the specimen S and the standard spectrum differ from each other as to the standard with respect to the energy value. When performing the curve fitting calculation process, the energy axis of the standard spectrum (or the energy axis of the Auger spectrum obtained from the specimen S) is shifted in order to correct the shift in energy axis (horizontal axis) that occurs due to the difference in the standard with respect to the energy value.

The abundance ratio of Cu in each chemical bonding state calculated from the X-ray-excited Auger spectrum illustrated in FIGS. 7 and 8 is listed in Table 2.

TABLE 2

|  | Cu | $Cu_2O$ | CuO |
| --- | --- | --- | --- |
| Before heating | 40% | 40% | 20% |
| After heating | 5% | 60% | 35% |

The chemical bonding state analysis section 66 calculates the quantitative value of the element in each chemical bonding state included in the specimen S based on the abundance ratio of the analysis target element in each chemical bonding state, and the quantitative value of each element included in the specimen S (step S18). The chemical bonding state analysis section 66 calculates the quantitative value of the analysis target element in each chemical bonding state by applying the abundance ratio of the analysis target element in each chemical bonding state calculated by the curve fitting calculation process (see Table 2) to the quantitative value of each element included in the specimen S that has been calculated by the photoelectron spectrum analysis section 64 (see Table 1).

The quantitative value of Cu in each chemical bonding state calculated by applying the abundance ratio of Cu in each chemical bonding state (see Table 2) to the quantitative value of each element included in the specimen S (see Table 1), is listed in Table 3.

TABLE 3

|  | C | O | Cu | $Cu_2O$ | CuO |
|---|---|---|---|---|---|
| Before heating | 31% | 23% | 18.6% | 18.6% | 9.2% |
| After heating | 40% | 35% | 1.25% | 15% | 8.75% |

The quantitative values of C, O, Cu, $Cu_2O$, and CuO included in the specimen S are listed in Table 3.

When it has been determined that the analysis target element is not a metal that belongs to the fourth or higher period of the periodic table (No in step S14), the chemical bonding state analysis section 66 performs the curve fitting process on the photoelectron spectrum by using a trial function (e.g., mixed Gaussian/Lorentzian function) (step S20). The chemical bonding state analysis section 66 calculates the quantitative value of the analysis target element in each chemical bonding state included in the specimen S from the results obtained by performing the curve fitting process on the photoelectron spectrum (step S18). Note that this process is not performed on the specimen S illustrated in FIGS. 2 to 5 since the analysis target element (Cu) is a metal that belongs to the fourth or higher period of the periodic table.

The quantitative value of the analysis target element in each chemical bonding state included in the specimen S can be calculated by performing the above process.

The analysis method according to one embodiment of the invention has the following features, for example.

Since the analysis method according to one embodiment of the invention calculates the quantitative value of the analysis target element in each chemical bonding state included in the specimen S by performing the curve fitting process on the X-ray-excited Auger spectrum by using the electron beam-excited Auger electron standard spectrum, it is possible to accurately calculate the quantitative value of the analysis target element in each chemical bonding state even when the analysis target element is a metal that belongs to the fourth or higher period of the periodic table. The reasons therefor are described below.

Since the photoelectron spectrum of a metal that belongs to the fourth or higher period is characterized in that the shift amount of each peak is small when the chemical bonding state has changed, it is difficult to apply the curve fitting process to the photoelectron spectrum of a metal that belongs to the fourth or higher period. On the other hand, the Auger spectrum of a metal that belongs to the fourth or higher period is characterized in that the shift amount of each peak is large when the chemical bonding state has changed. However, since the Auger spectrum has a complex shape, it is difficult to perform the curve fitting calculation process on the Auger spectrum by using a mixed Gaussian/Lorentzian function.

Since the analysis method according to one embodiment of the invention calculates the quantitative value of the analysis target element in each chemical bonding state included in the specimen S by performing the curve fitting process on the X-ray-excited Auger spectrum by using the electron beam-excited Auger electron standard spectrum, it is possible to accurately calculate the quantitative value of the analysis target element in each chemical bonding state even when the analysis target element is a that belongs to the fourth or higher period.

In the analysis method according to one embodiment of the invention, the step that calculates the quantitative value of the analysis target element in each chemical bonding state includes a step that performs the curve fitting process on the X-ray-excited Auger spectrum by using the electron beam-excited Auger electron standard spectrum, and calculates the abundance ratio of the analysis target element in each chemical bonding state (step S16), and a step that calculates the quantitative value of the analysis target element in each chemical bonding state based on the abundance ratio of the analysis target element in each chemical bonding state, and the quantitative value of each element included in the specimen S (step S18). Therefore, it is possible to calculate the quantitative value of the analysis target element in each chemical bonding state from the X-ray-excited Auger spectrum.

The X-ray photoelectron spectroscope 100 includes the spectrum acquisition section 62 that acquires a photoelectron spectrum and an X-ray-excited Auger spectrum, the photoelectron spectrum being obtained by detecting photoelectrons emitted from a specimen by irradiating the specimen S with X-rays, and the X-ray-excited Auger spectrum being obtained by detecting Auger electrons emitted from the specimen S by irradiating the specimen S with X-rays, the photoelectron spectrum analysis section 64 that calculates the quantitative value of each element included in the specimen S based on the photoelectron spectrum, and the chemical bonding state analysis section 66 that performs the curve fitting process on the X-ray-excited Auger spectrum by using the electron beam-excited Auger electron standard spectrum, and calculates the quantitative value of the analysis target element in each chemical bonding state included in the specimen S. The X-ray photoelectron spectroscope 100 can thus accurately calculate the quantitative value of the analysis target element in each chemical bonding state even when the analysis target element is a metal that belongs to the fourth or higher period.

The invention includes various other configurations substantially the same as the configurations described above in connection with the embodiments (e.g., a configuration having the same function, method, and results, or a configuration having the same objective and effects). The invention also includes a configuration in which an unsubstantial part described above in connection with the embodiments is replaced by another part. The invention also includes a configuration having the same effects as those of the configurations described above in connection with the embodiments, or a configuration capable of achieving the same objective as that of the configurations described above in connection with the embodiments. The invention further includes a configuration in which a known technique is added to the configurations described above in connection with the embodiments.

Although only some embodiments of the invention have been described in detail above, those skilled in the art would readily appreciate that many modifications are possible in the embodiments without materially departing from the novel teachings and advantages of the invention. Accordingly, all such modifications are intended to be included within the scope of the invention.

What is claimed is:

1. An analysis method comprising:
   acquiring a photoelectron spectrum and an X-ray-excited Auger spectrum, the photoelectron spectrum being obtained by detecting photoelectrons emitted from a specimen by irradiating the specimen with X-rays, and the X-ray-excited Auger spectrum being obtained by detecting Auger electrons emitted from the specimen by irradiating the specimen with X-rays;
   calculating a quantitative value of each element included in the specimen based on the photoelectron spectrum;
   performing a curve fitting process on the X-ray-excited Auger spectrum by using an electron beam-excited Auger electron standard spectrum, and calculating a quantitative value of an analysis target element in each chemical bonding state included in the specimen; and
   wherein the calculating of the quantitative value of the analysis target element in each chemical bonding state performs the curve fitting process on the X-ray-excited Auger spectrum by using the electron beam-excited Auger electron standard spectrum, and calculates the quantitative value of the analysis target element in each chemical bonding state when the analysis target element is a metal that belongs to the fourth or higher period of the periodic table.

2. The analysis method as defined in claim 1,
   wherein the calculating of the quantitative value of the analysis target element in each chemical bonding state comprises:
   performing the curve fitting process on the X-ray-excited Auger spectrum by using the electron beam-excited Auger electron standard spectrum, and calculating an abundance ratio of the analysis target element in each chemical bonding state; and
   calculating the quantitative value of the analysis target element in each chemical bonding state based on the abundance ratio of the analysis target element in each chemical bonding state, and the quantitative value of each element included in the specimen.

3. An X-ray photoelectron spectroscope comprising:
   a spectrum acquisition section that acquires a photoelectron spectrum and an X-ray-excited Auger spectrum, the photoelectron spectrum being obtained by detecting photoelectrons emitted from a specimen by irradiating the specimen with X-rays, and the X-ray-excited Auger spectrum being obtained by detecting Auger electrons emitted from the specimen by irradiating the specimen with X-rays;
   a photoelectron spectrum analysis section that calculates a quantitative value of each element included in the specimen based on the photoelectron spectrum;
   a chemical bonding state analysis section that performs a curve fitting process on the X-ray-excited Auger spectrum by using an electron beam-excited Auger electron standard spectrum, and calculates a quantitative value of an analysis target element in each chemical bonding state included in the specimen; and
   wherein the chemical bonding state analysis section performs the curve fitting process on the X-ray-excited Auger spectrum by using the electron beam-excited Auger electron standard spectrum, and calculates the quantitative value of the analysis target element in each chemical bonding state when the analysis target element is a metal that belongs to the fourth or higher period of the periodic table.

4. The X-ray photoelectron spectroscope as defined in claim 3,
   wherein the chemical bonding state analysis section performs a process that performs the curve fitting process on the X-ray-excited Auger spectrum by using the electron beam-excited Auger electron standard spectrum, and calculates an abundance ratio of the analysis target element in each chemical bonding state, and a process that calculates the quantitative value of the analysis target element in each chemical bonding state based on the abundance ratio of the analysis target element in each chemical bonding state, and the quantitative value of each element included in the specimen.

* * * * *